United States Patent [19]

Tener

[11] 4,427,005
[45] Jan. 24, 1984

[54] APPARATUS AND METHOD FOR TREATING BREAST TUMORS

[76] Inventor: William S. Tener, 69 Timberline Dr., Oreana, Ill. 62554

[21] Appl. No.: 354,597

[22] Filed: Mar. 4, 1982

[51] Int. Cl.³ ............................................. A61B 17/00
[52] U.S. Cl. ................................ 128/303 R; 128/1.2; 604/116
[58] Field of Search ............... 128/1.2, 303 B, 303 R, 128/329 A, 329 R, 654, 630, 1.1, 346; 604/116

[56] References Cited

U.S. PATENT DOCUMENTS

| | | |
|---|---|---|
| 1,093,112 | 4/1914 | Clarke . |
| 2,587,966 | 3/1952 | Cleary .................................. 128/346 |
| 3,061,936 | 11/1962 | De Dobbeleer ....................... 33/174 |
| 3,135,263 | 6/1964 | Connelley, Jr. ...................... 128/303 |
| 3,508,552 | 4/1970 | Hainault ............................... 128/303 |
| 3,655,191 | 4/1972 | Grant ................................. 273/1 G X |
| 3,750,653 | 8/1973 | Simon .................................... 128/1.2 |
| 3,811,426 | 5/1974 | Culver et al. ......................... 128/1.2 |
| 3,817,249 | 6/1974 | Nicholson ............................. 128/303 |
| 3,970,073 | 7/1976 | Greene ................................. 128/1.2 |
| 4,167,179 | 9/1979 | Kirsch .................................. 128/1.2 |
| 4,378,802 | 4/1983 | Ersek ................................... 128/346 |

OTHER PUBLICATIONS

Bernard Pierquin, et al., Radiation Therapy in the Management of Primary Breast Cancer, pp. 645–648, Am J Roentgenol 127: 645–648, 1976.

Primary Examiner—Kyle L. Howell
Assistant Examiner—Christine A. Fukushima
Attorney, Agent, or Firm—Wood, Dalton, Phillips, Mason & Rowe

[57] ABSTRACT

A template for controlling the location and guiding of needles in a patient's breast preparatory to placement of radioactive seeds. The template has a pair of template blocks, each having a plurality of pre-drilled needle holes arranged in the same pattern and a template bridge adjustably connected to the top thereof to hold the template blocks with the needle holes in alignment. A shell having a part shaped to a portion of the patient's breast is adjustably fixed to the template for orienting the template blocks to the patient's breast whereby needles can be passed through the pre-drilled needle holes at predetermined locations and in a predetermined pattern. The method of treating breast tumors comprises the use of the template with the placement of a control mark on the patient's skin to denote the center of the field to be treated and the formation of the shell to conform to a portion of the patient's breast with a reference mark placed thereon corresponding to the location of the control mark for proper alignment of the shell part with the patient's breast and, thereafter, locking the shell to the template while the control and reference marks remain coincident and the pre-drilled needle holes are oriented in the desired manner for placement of the needles.

9 Claims, 4 Drawing Figures

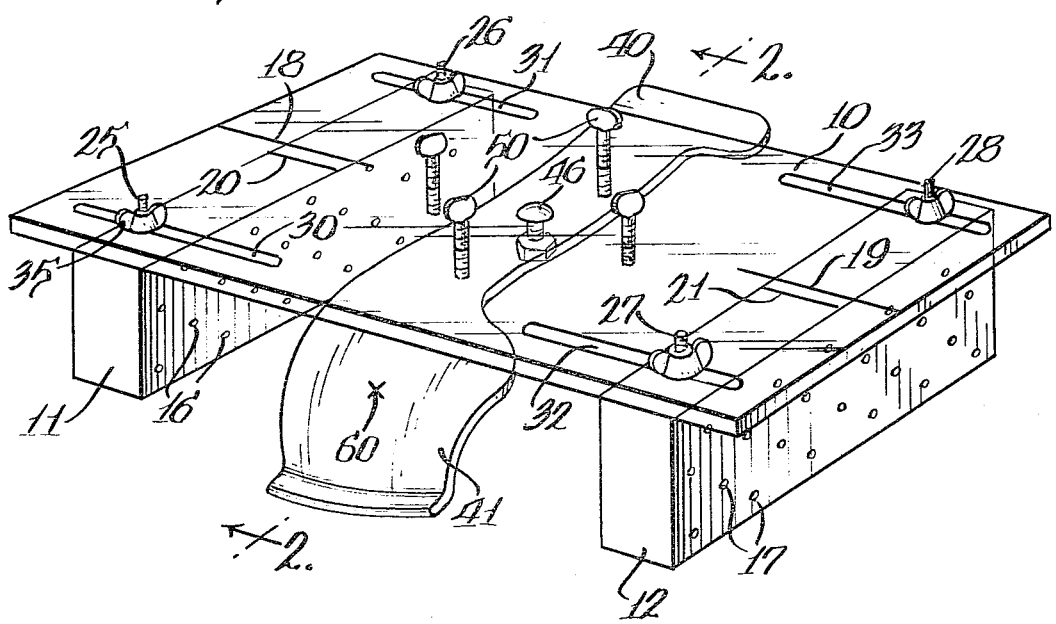
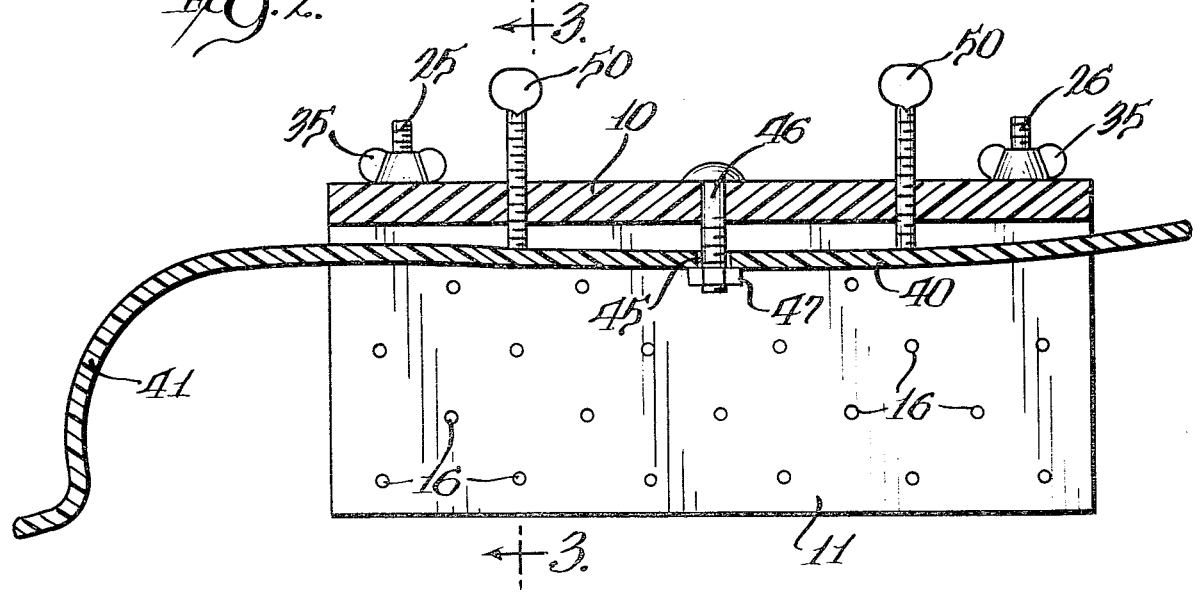

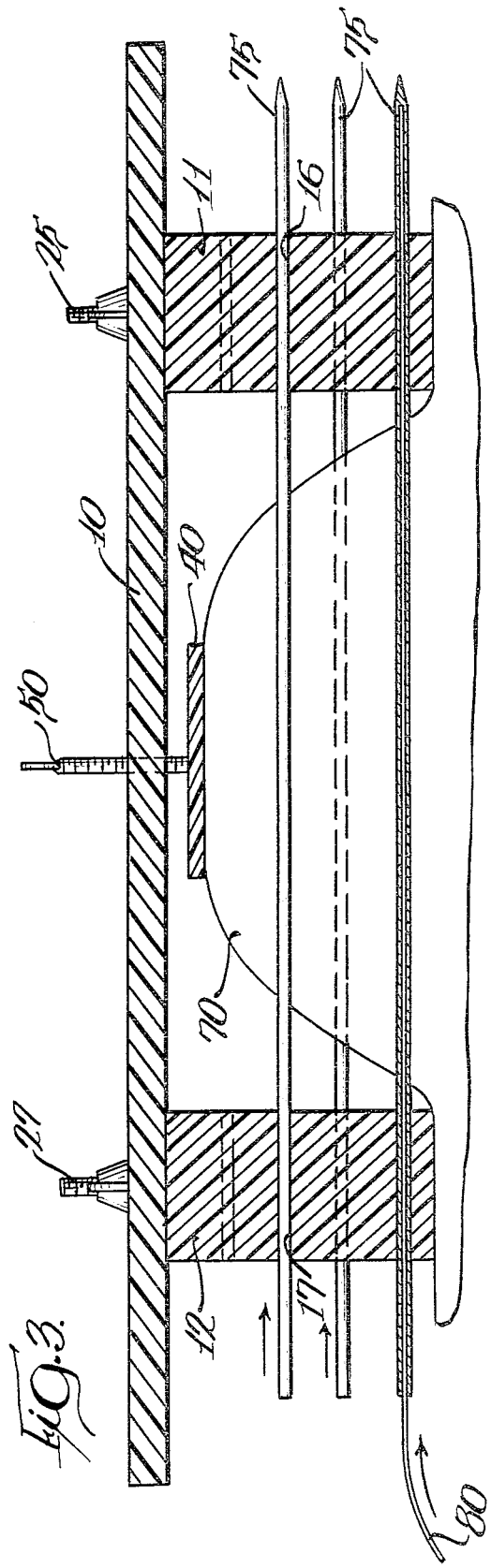
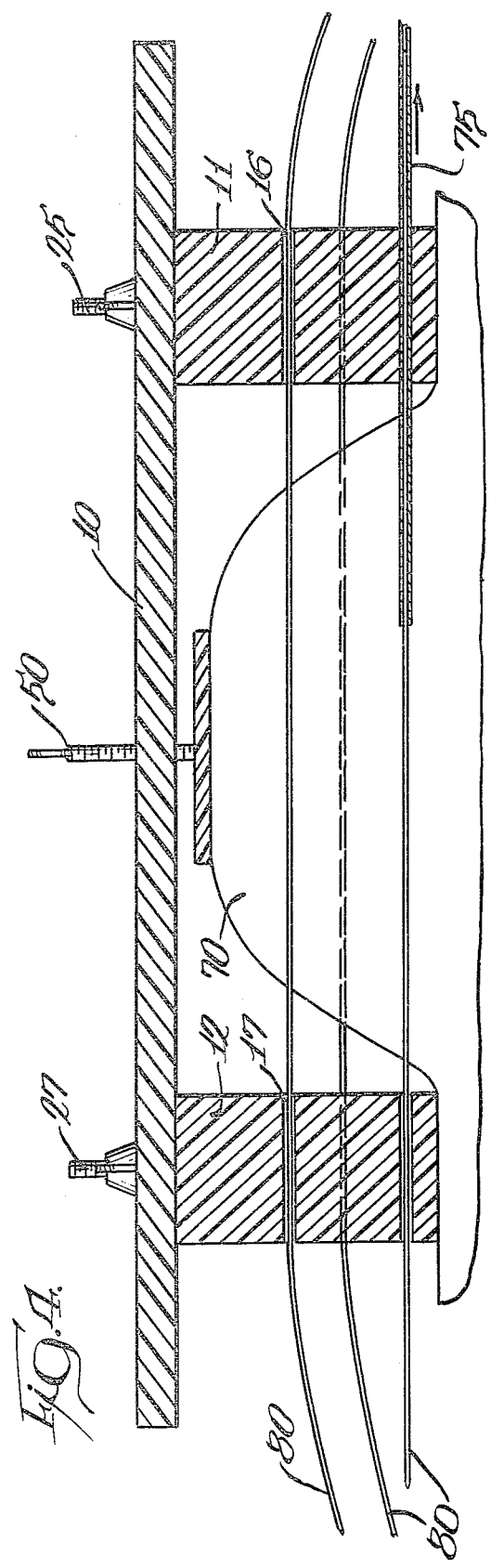

APPARATUS AND METHOD FOR TREATING BREAST TUMORS

BACKGROUND OF THE INVENTION

This invention pertains to a structure for improving the placement of needles in a patient's breast and, thereby, the subsequent placement of radioactive seeds with considerably greater accuracy than heretofore known. The invention also relates to an improved method of treating breast tumors.

The use of $^{192}$Iridium in effectively treating breast tumors has become well known. The radioactive seeds are implanted in the patient's breast through a series of steps including the passage of a predetermined number of needles through the breast at predetermined locations and in a predetermined pattern. After all the desired needles are placed, Nylon tubing is passed through the needles and the needles are then withdrawn by sliding over the tubing. The radioactive seeds can then be inserted into the Nylon tubing. It has been known to guide a series of needles to and through a patient's breast by independent templates through which the needles extend and which are located at opposite sides of the volume to be treated.

The prior art has not optimized the placement of the needles and, thereby, subsequent positioning of the radioactive seeds with respect to the center of the mass or field which the therapist wishes to treat.

SUMMARY OF THE INVENTION

A primary feature of the invention is to provide a method of treating breast tumors utilizing a template for guidance of needle placement through a patient's breast wherein a shell has a part conforming to a portion of the patient's breast and which is associated with the template to guide and maintain the template with pre-drilled needle holes in desired alignment with the patient's breast. The needles are passed through aligned needle holes in both of a pair of template blocks positioned at opposite sides of the volume to be treated followed by substituting tubing for the needles, which tubing receives radioactive seeds.

Still another feature of the invention is to provide a method of treating breast tumors comprising the steps of placing a control mark on the patient's skin to denote the center of the field to be treated, forming a shell with a part conforming to a portion of the patient's breast encompassing said mark and placing a reference mark on said part, placing said shell part on the patient's breast in a position to have said reference mark coincident with said control mark, mounting said shell to the bridge of a template, said template having a pair of spaced-apart template blocks depending from said bridge and with pre-drilled needle holes therein which are aligned in said two blocks, orienting said template relative to said shell for desired needle placement through the breast by passage through the needle holes while maintaining said control and reference marks coincident, fixing the position of the shell relative to the template with the template above the breast, passing the desired needles through said needle holes, and thereafter substituting tubing for the needles, which tubing receives radioactive seeds.

Another feature of the invention relates to a structure for accurate placement of a plurality of needles in a patient's breast comprising a template having a pair of template blocks, with each block having a plurality of pre-drilled needle holes arranged in the same pattern, and a template bridge adjustably connected to the top of each of said template blocks to hold said template blocks in spaced-apart relation with the needle holes of the two template blocks in alignment. The template bridge overlies a patient's breast with the template blocks positioned one at each side of the volume to be treated. A shell having a part shaped to conform to a portion of the patient's breast is locked in oriented relation to the template to maintain the template in a desired position relative to the shell. Orientation of the shell with the patient's breast assures controlled passage of the needles through the needle holes in the blocks and the patient's breast.

BRIEF DESCRIPTION OF THE DRAWINGS

FIG. 1 is a perspective view of the template and shell associated therewith;

FIG. 2 is a vertical section, taken generally along the line 2—2 in FIG. 1 and on an enlarged scale;

FIG. 3 is a sectional view, taken generally along the line 3—3 in FIG. 2 and showing the template and shell in association with a patient's breast and showing a series of needles in position and with Nylon tubing being inserted into one of said needles; and FIG. 4 is a view, similar to FIG. 3, showing optional placement of the template and shell during placement of the tubing.

DESCRIPTION OF THE PREFERRED EMBODIMENT

The template is shown generally in FIG. 1 and has a template bridge 10 formed of a rigid transparent plastic material, such as a cast acrylic sheet, and a pair of template blocks 11 and 12 formed of relatively thick sections of the same material as the template bridge. Each of the template blocks has a plurality of pre-drilled needle holes 16 and 17, respectively, which have the same pattern in each of the template blocks and which can be arranged to meet the requirements of the therapist. One of the functions of the template bridge 10 is to hold the template blocks 11 and 12 in properly-aligned relation whereby the needle holes 16 and 17 will be aligned. This is accomplished by the use of sight lines 18 and 19 on the template bridge which align with sight lines 20 and 21 on top of the template blocks and which are visible through the transparent template bridge. The template blocks are held in fixed relation to the template bridge by a series of bolts 25–28 extending upwardly from the tops of the template blocks and embedded therein. These bolts extend through a series of elongate slots 30–33 formed in the template bridge and associated one with each of the bolts. This enables adjustment in the spacing between the template blocks as well as alignment of the sight lines 18 and 19 with the sight lines 20 and 21 and, thereafter, the template blocks can be secured to the template bridge by tightening the wing nuts 35 associated one with each of the bolts.

A shell 40 having a part 41 conforming to a portion of the patient's breast is adjustably associated with the template by having an opening 45 loosely receiving a bolt 46 which extends downwardly from the middle of the template bridge 10 with the shell being retained on the bolt by a nut 47. The shell 40 can be locked to the template in a selected position relative thereto by tightening the nut 47 and downwardly advancing two or more of a series of thumb set screws 50 which are threaded through the template bridge 10 and having parts extending downwardly to contact the upper side of the shell, as shown in FIG. 2.

In the method of treating breast tumors utilizing the template and shell, there are certain preoperative procedures relating primarily to forming of the shell part 41. This shell is preferably of a relatively thin plastic material, such as cast acrylic sheet, which is thermoplastic and can be softened by heat. The series of steps includes placing a control mark on the patient's skin with a skin marker utilizing a transferable ink and which denotes the center of the mass or field which the therapist wishes to treat. A mold of this area of the patient's breast is obtained with dental impression materials and the ink of the skin marker is transposed to the mold and is redefined on the mold with the skin marker for clarity, and then a plaster model is made from the mold. The plaster model represents the surface anatomy of the patient and the control mark is visible. The shell part 41 is softened by heat and adapted to the plaster model over an area including the control mark and the shell part 41 is then marked with a reference mark as defined by the "x" shown at 60 in FIG. 1 directly over the control mark as appearing on the plaster model.

In the operating room, the shell 40 is positioned to have the shell part 41 thereof positioned over a portion of the patient's breast with the reference mark 60 on the shell part 41 directly over the control mark on the patient's skin. The desired angles and directions for passage of the needles through the pre-drilled needle holes 16 and 17 are determined. The template blocks 11 and 12 with the desired arrangement or pattern of pre-drilled needle holes is selected and assembled with the template bridge 10 and the template bridge is then connected to the shell by the bolt 46 extending through the shell opening 45. The shell part 41 is then properly oriented on the patient's breast with the control and reference marks coincident and the template blocks positioned at opposite sides of the volume to be treated with the pre-drilled needle holes properly aligned for the passage of the needles. The nut 47 is tightened and the thumb set screws 50, which overlie the shell, are threaded downwardly into firm engagement with the upper side of the shell.

The general orientation of the structure may be as viewed in FIG. 3, with the patient's breast illustrated at 70. With the template and shell properly oriented and held in position, a series of needles 75 are advanced through selected pre-drilled needle holes 17 in the template block 12 which defines the entry side of the template and, after passage through the breast, pass through pre-drilled needle holes 16 in the template block 11 at the exit side. After placement of the needles, Nylon tubing is passed through a major part of the length of the needles and beyond the template block 11 at the exit side, with the insertion of one length of tubing 80 being shown in FIG. 3. The needles are then withdrawn by sliding over the lengths of tubing 80 disposed therein, with this stage of the procedure shown in FIG. 4 wherein a last of the needles 75 is being withdrawn. Subsequently, the Nylon tubes may be secured from being withdrawn from the patient by placing vinyl retaining strips on the tubing at each of the exposed ends thereof and which also functions to keep the tubes equidistant as the patient moves during treatment. At the appropriate time, thereafter, the patient can be awakened and the tubing later loaded with radioactive seeds as is customary.

From the foregoing, it will be evident that the template and shell provide a structure which results in an effective and simple method for obtaining optimal geometry on nearly all breast implants. There can be a variety of template blocks available having pre-drilled needle holes in anywhere from three to five planes in a staggered configuration with the separation between the needle holes being equidistant. The needle holes 17 in the entry side template block 12 accommodate the needles 75 snugly and the length of the needle holes in the template block insures that the needles travel as straight a path as possible through the breast tissue. As stated previously, the needle holes 16 in the template block 11 at the exit side are in a matching pattern to those in the template block 12 and receive the needles after their exit from the breast.

In a preferred form, the shell part 41 covers about one-third of the total width of the breast from the supraclavicular fossa to the inframammary fold. Obviously, the shell part 41 is limited in size to not cover more of the breast than is necessary in order to permit the desired plane of needle passage through the breast.

The method has been described with the template in place during insertion of the Nylon tubing 80 within the needles, as shown in FIG. 4. However, it would also be possible to remove the template and shell by endwise withdrawal of the template blocks from the needles and, thereafter, insert the Nylon tubing within the needles.

Excellent constancy of needle separation and staggering of needle planes is achieved in even the largest of implant volumes. The accurate delivery of radiation to the desired tumor volume is obtained with minimization of "hot" or "cold" spots.

I claim:

1. A method of treating breast tumors comprising the steps of placing a control mark on the patient's skin to denote the center of the field to be treated, forming a shell with a part conforming to a portion of the patient's breast encompassing said mark and placing a reference mark on said part, placing said shell part on the patient's breast in a position to have said reference mark coincident with said control mark, mounting said shell to the bridge of a template, said template having a pair of spaced-apart template blocks depending from said bridge and with pre-drilled needle holes therein which are aligned in said two blocks, orienting said template relative to said shell for desired needle placement through the breast by passage through the needle holes while maintaining said control and reference marks coincident, fixing the position of the shell relative to the template with the template above the breast, passing the desired needles through said needle holes, and thereafter substituting tubing for the needles which tubing receives radioactive seeds.

2. A method as defined in claim 1 wherein said shell is of formable plastic and said part is formed by the steps of: forming a mold of said breast portion, forming a model of said breast portion from said mold, and shaping said plastic to said model.

3. A method as defined in claim 2 wherein said shell plastic is transparent and the control mark is made by a transferable ink which transfers to said mold and which is re-inked for transfer to said model, said transfer mark being applied to the shell part by viewing through the shell the mark as appearing on the model.

4. A method of placing needles preparatory to treatment of breast tumors comprising the steps of formin a shell to conform to a portion of the patient's breast, placing said shell on the patient's breast in a predetermined position, associating said shell with the bridge of a template, said template having a pair of spaced-apart template blocks depending from said bridge and with pre-drilled needle holes therein which are aligned in said two blocks, orienting said template relative to said shell for desired needle placement through the breast by passage through the needle holes, fixing the position of the shell relative to the template with the template above the breast, and passing the desired needles through said needle holes.

5. Structure for accurate placement of a plurality of needles in a patient's breast comprising, a template having a pair of template blocks, each of the template blocks having a plurality of pre-drilled needle holes arranged in the same pattern in each template block, and a template bridge adjustably connected to the top of each of said template blocks to hold said template blocks in spaced-apart relation with said needle holes of the two template blocks in alignment whereby said template bridge may overlie the patient's breast with the template blocks positioned one at each side of the portion of the breast to be treated, and said template is adapted to be located relative to the patient's breast by a shell having a part shaped to conform to a portion of the patient's breast, means for adjustably mounting said shell to the template bridge, and means for securely locking the shell to the template bridge in adjusted position.

6. A structure as defined in claim 5 wherein said template blocks have exposed bolts at the tops thereof which are partially embedded in said blocks, said template bridge having elongate slots to adjustably receive said bolts, and wing nuts threadable on said bolts for locking the template blocks to the template bridge.

7. A structure as defined in claim 6 wherein said template bridge and template blocks are of transparent material and include sight lines thereon to facilitate alignment of said template blocks.

8. A structure as defined in claim 5 wherein said shell is made of a formable plastic which can be formed into said conforming shape.

9. A structure as defined in claim 5 wherein said adjustable means for mounting the shell is a threaded member depending from the template bridge at the middle thereof, and said locking means are a nut threaded on the threaded member and a plurality of thumb set screws threaded in the template bridge and extending therebeneath to engage said shell.

* * * * *